United States Patent [19]

Mohr et al.

[11] 3,939,828
[45] Feb. 24, 1976

[54] METHOD AND CLASP FOR INTERNAL OSSEOUS FIXATION

[76] Inventors: Robert N. Mohr, 1350-9th Ave.; Howard J. Zlotoff, 1341-12th Ave., both of San Francisco, Calif. 94122

[22] Filed: Sept. 9, 1974

[21] Appl. No.: 504,052

[52] U.S. Cl. .......................... 128/92 B; 128/334 R
[51] Int. Cl.² ............................................ A61F 5/04
[58] Field of Search ............ 128/92 B, 92 R, 92 EA, 128/83, 334, 337, 335, 336; 24/87 C, 73 ES; 85/49, 13

[56] References Cited
UNITED STATES PATENTS

| | | | |
|---|---|---|---|
| 2,898,741 | 8/1959 | Milliken | 24/87 C |
| 3,807,394 | 4/1974 | Attenborough | 128/92 B |

*Primary Examiner*—J. D. Yasko
*Attorney, Agent, or Firm*—Julian Caplan

[57] ABSTRACT

A clasp formed of spring material is Z-shaped in top plan and in side elevation shows two legs which converge downwardly at about a 15° angle, one leg depending from each end of the Z. In end elevation the legs are perpendicular to the horizontal portion of the clasp. To install the clasp, bone segments are manually or mechanically manipulated to desired position. A hole is drilled on each side of the osteotomy equidistant therefrom at an angle of about 15° from the perpendicular, and converging toward the osteotomy preferably using a template which determines hole locations, dependent on the size of clasp selected. One leg of the clasp is inserted in one hole. The other leg is pulled toward the other hole, preferably using an instrument with a hook-like extremity. As the second leg is pulled into position the clasp is stressed, the Z shape spreading apart; and after the clasp is fully installed, the resiliency of the clasp applies a continuous force compressing the bone segments with a constant force and immobilizing same.

5 Claims, 8 Drawing Figures

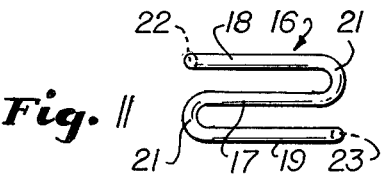
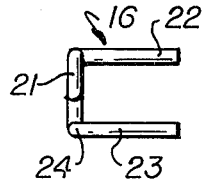
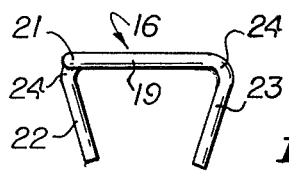
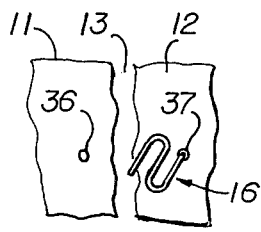
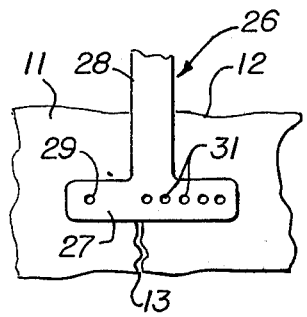
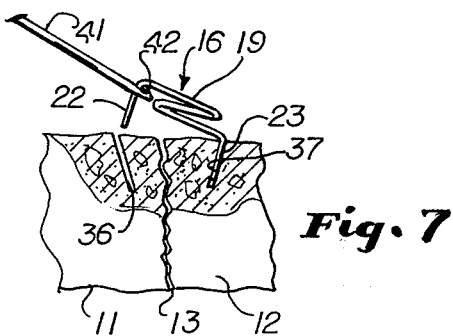
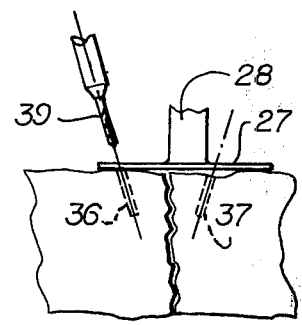
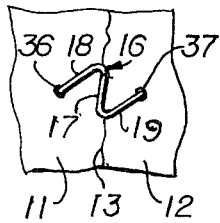

METHOD AND CLASP FOR INTERNAL OSSEOUS FIXATION

This invention relates to a new and improved clasp for internal osseous fixation. The clasp is formed of a spring-like surgical quality steel which is compatible with body tissues and allows for conventional sterilization techniques. The clasp is rapidly inserted in a variety of bone location, as hereinafter described in detail, eliminating other time consuming methods of internal fixation while developing immobilization of the bone segments with a constant compressive force promoting early healing.

One feature of the advantage of the present invention is the fact that the clasp is biologically compatible with surrounding bone and soft tissues.

Another advantage of the invention is the fact that it may be rapidly inserted, whereas conventional techniques of the prior art are more time consuming.

A still further advantage of the invention is the fact that the clasp develops constant compressive force, within physiological limits, thus promoting early healing at the site of application.

A still further advantage of the invention is that it continually maintains bone alignment established at the time of the surgery.

Another feature of the invention is the fact that the clasp is radiopaque so that x-ray evaluation of the placement may be made.

The converging legs of the clasp reduce the risk of dislodgement after insertion.

Resterilization, if the clasp is contaminated, may be performed.

Another advantage of the invention is the fact that the placement is completely internal, eliminating the necessity of removal once bone healing occurs.

Other objects of the present invention will become apparent upon reading the following specification and referring to the accompanying drawings in which similar characters of reference represent corresponding parts in each of the several views. In the drawings:

FIG. 1 is a top plan view of a clasp in accordance with the present invention shown in unstressed condition.

FIG. 2 is a side elevation thereof.

FIG. 3 is an end elevation thereof.

FIG. 4 is a schematic view partly broken away in section showing bone segments separated by an osteotomy in the position at the beginning of the operation and also showing a template used in preparation of the bone segments as a guide for drilling locating holes.

FIG. 5 is a side elevational view of the structure of FIG. 4 showing drilling of the hole through the template.

FIG. 6 shows insertion of one leg of the clasp in one of the holes drilled in the bone.

FIG. 7 shows schematically the pulling of the clasp by means of an instrument to stretch the clasp preparatory to inserting the other leg in the opposite hole.

FIG. 8 shows the clasp in place at the completion of the operation.

Illustrated herein are first bone segment 11 and second bone segment 12 separated by an osteotomy 13 which may have been created by fracture or by surgery. The bone segments are brought together by manual or mechanical manipulation as close as possible and aligned and opposed. The surgeon then estimates the proper size clasp 16 to be used, the sizes of clasps varying from about 8 millimeters to 16 millimeters in overall length. Preferably, the clasp is inserted in an area of the bone which is flat rather than over a ridge or convexity so that it lies flat after insertion.

Clasp 16 in its unstressed condition is shown in FIGS. 1–3. Viewed in top plan, as in FIG. 1, there is a central horizontal stretch 17 and approximately parallel thereto are first and second horizontal stretches 18, 19, respectively, each jointed to the central stretch 17 by a U-bend 21. At the opposite end of stretches 18 and 19 are first and second legs 22, 23, respectively, joined to stretches 18, 19 by approximately 75° bends 24. As best shown in FIG. 2, the legs 22, 23 converge downwardly when viewed in side elevation, each varying from the vertical by an angle of approximately 15°. As viewed in end elevation in FIG. 3, the legs 22,23 are parallel and perpendicular to the plane of stretches 17–19. The diagonal distance between legs 22, 23, as viewed in FIG. 1, determines the size of the clasp; and, as has been stated, such size varies between 8 millimeters and 16 millimeters.

Preparatory to installation of clasp 16, a template 26 is preferably used for the purpose of locating the drill sites, it being understood that other templates or visual approximation may be used. The holes to be drilled are to be spaced apart a distance at least two millimeters greater than the distance between legs 22, 23 in the unstressed position of the clasp and not greater than four millimeters. Template 26 has a plate 27 and central handle 28 integral therewith or attached thereto. Handle 28 preferably angles at about 45° away from the plane of plate 27. A first locating hole 29 is formed on one side of the plate 27. On the opposite side of plate 27 is a series of second locating holes 31 at varying known distances from hole 29. The template 26 is located relative to the fracture 13, as viewed in FIG. 4. A hole 31 is selected depending on the size clasp 16 to be inserted. Template 16 is positioned so that holes 29 and selected hole 31 are equidistant from osteotomy 13. Further, as has previously been mentioned, the holes are approximately two to four millimeters farther apart than the legs 22, 23. The drill 39 selected is preferably between 0.045 and 0.052 inch in diameter and the holes are drilled at an angle of 15° from the perpendicular directed toward the osteotomy site. Thereupon, the template is removed.

Directing attention to FIG. 6, one of the legs of clasp 16 is inserted in hole 37, as shown the leg selected being leg 23. As shown in FIG. 7, a puller instrument 41 having a hook 42 at its distal end is used to stretch the clasp 16. The hook 42 is placed around leg 22 at its most superior aspect. While maintaining pressure on the inserted leg 23 with the thumb of one hand, the puller 41 is used to stretch the clasp apart with a steady pull toward the hole 36. Leg 22 is then inserted in hole 36 and the puller 41 removed. The clasp 16 is then under tension and is finally positioned by pressing down until the stretches 17–19 are flat on the bone surface. At the completion of this operation, as shown in FIG. 8, it will be seen that the angle between stretches 18 and 19 and central stretch 17 have increased and that the stretches 18, 19 are no longer parallel to each other. Since the clasp 16 is of a resilient material, the clasp is under tension thus immobilizing the opposed and aligned bone segments with a constant compressive force.

To complete the operation, soft tissue should be interposed between the clasp and the skin.

What is claimed is:

1. A clasp for osseous fixation formed of a unitary piece of resilient wire and having a horizontal portion formed of first, second and third stretches, a first 180° bend interconnecting a first end of said first stretch with a first end of said second stretch, a second 180° bend interconnecting a second end of said second stretch with a first end of said third stretch, said first, second and third stretches in the unstressed condition of said clasp being substantially parallel to each other and being of substantially identical lengths, a first leg depending from a second end of said first stretch, a second leg depending from a second end of said third stretch, said legs being located on diagonal corners of said clasp, said legs converge and each said leg is disposed at an acute angle relative to said horizontal portion said horizontal portion being stressed when said legs are pulled away from each other by increasing the arcuate extents of said bends, said legs being remote from each other so that said legs may be inserted in holes drilled in bone segment on opposite sides of an osteotomy or fracture.

2. A clasp according to claim 1 and a template, said template having a plate formed with a first hole and a plurality of spaced second holes remote from said first hole and a handle extending outward away from said plate, said holes all lying along a straight line, said first hole and the second hole closest to said first bore being spaced apart a distance substantially greater than the distance between said first and second legs when said clasp is unstressed, said first and one of said second holes being adapted for use as guides in drilling holes in the bone segments.

3. A clasp according to claim 1 and a puller instrument having a handle and a shank formed with a hook whereby when said first leg is adapted to be inserted in a first hole in a first bone fragment, said second leg may be pulled by said hook away from said first leg for insertion of said second leg in a second hole in a bone fragment on the opposite side of an osteotomy by placing said hook around said second leg and pulling said handle in a direction away from said first hole in a direct line between said holes.

4. A method of osseous fixation comprising drilling a first hole in a bone fragment on a first side of an osteotomy, drilling a second hole in a bone fragment on a second side of an osteotomy opposite said first side, providing a clasp in accordance with claim 1, said first and second holes being spaced apart a greater distance than said first and second legs when said clasp is in unstressed condition, inserting said first leg in said first hole, and stressing said clasp by pulling said second leg away from said first leg until said second leg fits into said second hole, said clasp when stressed being disposed with said second stretch disposed at acute angles to said first and second stretches.

5. The method claim 4 wherein said first and second holes are slanted toward said osteotomy and said legs are slanted in complementary direction.

* * * * *